US00PP28690P3

(12) United States Plant Patent
Volmary

(10) Patent No.: US PP28,690 P3
(45) Date of Patent: Nov. 21, 2017

(54) ***SUTERA* PLANT NAMED 'VOLSUT 2302'**

(50) Latin Name: *Sutera diffusus*
Varietal Denomination: VOLSUT 2302

(71) Applicant: Hubertus Volmary, Muenster (DE)

(72) Inventor: Hubertus Volmary, Muenster (DE)

(73) Assignee: Volmary GmbH, Muenster (DE)

( * ) Notice: Subject to any disclaimer, the term of this patent is extended or adjusted under 35 U.S.C. 154(b) by 8 days.

(21) Appl. No.: 14/999,187

(22) Filed: Apr. 8, 2016

(65) Prior Publication Data

US 2017/0295710 P1 Oct. 12, 2017

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Susan McCormick Ewoldt
(74) *Attorney, Agent, or Firm* — C. A. Whealy

(57) ABSTRACT

A new and distinct cultivar of *Sutera* plant named 'VOLSUT 2302', characterized by its compact, mounding and trailing plant habit; vigorous growth habit; freely branching habit; early and freely flowering habit; and relatively large white-colored flowers.

1 Drawing Sheet

Botanical designation: *Sutera diffusus*.
Cultivar denomination: 'VOLSUT 2302'.

BACKGROUND OF THE INVENTION

The present invention relates to a new and distinct cultivar of *Sutera* plant, botanically known as *Sutera diffusus* and hereinafter referred to by the name 'VOLSUT 2302'.

The new *Sutera* plant is a product of a planned breeding program conducted by the Inventor in Muenster, Germany. The objective of the breeding program is to create new compact and freely branching *Sutera* plants with numerous large flowers.

The new *Sutera* plant originated from an open-pollination in 2012 in Muenster, Germany of an unnamed proprietary selection of *Sutera diffusus*, not patented, as the female, or seed, parent with an unknown selection of *Sutera diffusus* as the male, or pollen, parent. The new *Sutera* plant was discovered and selected by the Inventor as a flowering plant from within the progeny of the stated open-pollination in a controlled greenhouse environment in Muenster, Germany in 2013.

Asexual reproduction of the new *Sutera* plant by terminal cuttings in a controlled greenhouse environment in Muenster, Germany since 2014, has shown that the unique features of this new *Sutera* plant are stable and reproduced true to type in successive generations.

SUMMARY OF THE INVENTION

Plants of the new *Sutera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'VOLSUT 2302'. These characteristics in combination distinguish 'VOLSUT 2302' as a new and distinct *Sutera* plant:

1. Compact, mounding and trailing plant habit.
2. Vigorous growth habit.
3. Freely branching habit.
4. Early and freely flowering habit.
5. Relatively large white-colored flowers.

Plants of the new *Sutera* can be compared to plants of the female parent selection. Plants of the new *Sutera* differ primarily from plants of the female parent selection in the following characteristics:

1. Plants of the new *Sutera* are not as trailing as plants of the female parent selection.
2. Plants of the new *Sutera* are more freely flowering than plants of the female parent selection.
3. Plants of the new *Sutera* have larger flowers than plants of the female parent selection.

Plants of the new *Sutera* can be compared to plants of the *Sutera cordata* 'SBAWH03-2', disclosed in U.S. Plant Pat. No. 23,881. In side-by-side comparisons conducted in Muenster, Germany, plants of the new *Sutera* differ primarily from plants of 'SBAWH03-2' in the following characteristics:

1. Plants of the new *Sutera* are not as trailing as plants of 'SBAWH03-2'.
2. Plants of the new *Sutera* have larger and darker green-colored leaves than plants of 'SBAWH03-2'.
3. Plants of the new *Sutera* have slightly larger flowers than plants of 'SBAWH03-2'.

BRIEF DESCRIPTION OF THE PHOTOGRAPH

The accompanying colored photograph illustrates the overall appearance of the new *Sutera* plant showing the colors as true as it is reasonably possible to obtain in colored reproductions of this type. Colors in the photograph may differ slightly from the color values cited in the detailed botanical description which accurately describe the colors of the new *Sutera* plant.

The photograph is a side perspective view of a typical flowering plant of 'VOLSUT 2302' grown in a container.

DETAILED BOTANICAL DESCRIPTION

The aforementioned photograph and following observations and measurements describe plants grown during the spring in 12-cm containers in a glass-covered greenhouse in Muenster, Germany and under commercial practices typical of commercial *Sutera* production. During the production of the plants, day temperatures ranged from 16° C. to 25° C., night temperatures ranged from 14° C. to 16° C. and light levels ranged from 5 to 65 klux. Plants were pinched two to three weeks after planting and were six months old when the photograph and the description were taken. In the following description, color references are made to The Royal Horticultural Society Colour Chart, Sixth Edition, except where general terms of ordinary dictionary significance are used.

Botanical classification: *Sutera diffusus* 'VOLSUT 2302'.

Parentage:

*Female, or seed, parent*.—Unnamed proprietary selection of *Sutera diffusus*, not patented.

*Male or pollen parent*.—Unknown selection of *Sutera diffusus*, not patented.

Propagation:

*Type*.—By terminal cuttings.

*Time to initiate roots, summer*.—About one to two weeks at temperatures ranging from about 20° C. to 25° C.

*Time to initiate roots, winter*.—About two to three weeks at temperatures ranging from about 15° C. to 23° C.

*Time to produce a rooted young plant, summer*.—About three weeks at temperatures ranging from about 20° C. to 25° C.

*Time to produce a rooted young plant, winter*.—About 30 days at temperatures ranging from about 15° C. to 23° C.

*Root description*.—Fine, fibrous; yellowish white in color.

*Rooting habit*.—Freely branching; medium density.

Plant description:

*Plant and growth habit*.—Compact, mounding and trailing plant habit; vigorous growth habit.

*Plant height*.—About 18 cm.

*Plant diameter* (*area of spread*).—About 50 cm.

Lateral branch description:

*Branching habit*.—Freely branching habit; when pinched, about 50 to 60 lateral branches develop per plant.

*Length*.—About 11 cm to 21 cm.

*Diameter*.—About 2 mm.

*Internode length*.—About 1.2 cm to 1.8 cm.

*Strength*.—Moderately strong to strong.

*Texture and luster*.—Slightly pubescent; matte.

*Color*.—Close to 142B to 142C.

Leaf description:

*Arrangement*.—Opposite, simple.

*Length*.—About 3.6 cm.

*Width*.—About 3.4 cm.

*Shape*.—Elliptic.

*Apex*.—Acute.

*Base*.—Acuminate.

*Margin*.—Serrate.

*Texture, upper and lower surfaces*.—Pubescent; velvety.

*Venation pattern*.—Pinnate, arcuate.

*Color*.—Developing leaves, upper surface: Close to 137C. Developing leaves, lower surface: Close to 146C. Fully expanded leaves, upper surface: Close to 144A; venation, close to 145A. Fully expanded leaves, lower surface: Close to 146C; venation, close to 145A.

*Petioles*.—Length: About 2 mm. Diameter: About 2 mm. Texture, upper and lower surfaces: Sparsely pubescent; slightly velvety. Color, upper and lower surfaces: Close to 146C.

Flower description:

*Flower arrangement*.—Relatively large single rotate and salverform flowers; freely flowering habit with potentially about 470 to 540 flowers developing per plant during the flowering season; flowers face mostly upright to slightly pendulous.

*Fragrance*.—None detected.

*Flowering habit*.—Early flowering habit, plants begin flowering about ten to twelve weeks after planting and flower recurrently year-round in the greenhouse.

*Flower longevity*.—Flowers last about seven days on the plant; flowers persistent.

*Flower diameter*.—About 2.7 cm.

*Flower length* (*height*).—About 2.7 cm.

*Throat diameter*.—About 2 mm.

*Tube length*.—About 2 cm.

*Tube diameter, at the base*.—About 0.7 mm.

*Flower buds*.—Length: About 5 mm. Diameter: About 3 mm. Shape: Roughly spatulate. Color: Close to 145C.

*Petals*.—Quantity and arrangement: Five per flower in a single whorl; fused at the base. Lobe length: About 2.7 cm. Lobe width: About 1 cm. Lobe shape: Orbicular. Lobe apex: Obtuse, rounded. Lobe margin: Entire. Texture and luster, petal lobes, upper and lower surfaces: Smooth, glabrous; velvety; matte. Texture, throat: Smooth. Texture, tube: Pubescent. Color: Petal lobes, when opening, upper and lower surfaces: Close to NN155D. Petal lobes, fully opened, upper and lower surfaces: Close to NN155D; color does not change with development. Throat: Close to 145D. Tube: Close to 15A.

*Sepals*.—Quantity and arrangement: Five per flower in a single whorl; fused at the base. Length: About 8 mm. Width: About 1 mm. Shape: Lanceolate. Apex: Acute. Margin: Entire. Texture, upper and lower surfaces: Pubescent. Color, upper and lower surfaces: Close to 141C.

*Peduncles*.—Length: About 6 mm. Diameter: About 1 mm. Angle: Upright to outwardly. Strength: Moderately strong to strong. Texture: Slightly pubescent. Color: Close to 146C.

*Reproductive organs*.—Androecium: Quantity of stamens per flower: About four. Filament length: About 1.5 cm. Filament color: Close to NN155D. Anther shape: Cylindrical. Anther length: About 1.5 mm. Anther color: Close to 14A. Amount of pollen: Moderate. Pollen color: Close to 12A. Gynoecium: Quantity of pistils per flower: One. Pistil length: About 1.4 cm. Style length: About 1.1 cm. Style color: Close to 14A. Stigma shape: Rounded, undulate. Stigma color: Close to 14A. Ovary color: Close to 14A.

*Seeds & fruits*.—Seed and fruit production have not been observed on plants of the new *Sutera*.

Garden performance: Plants of the new *Sutera* have been observed to have good garden performance and to tolerate wind, rain and temperatures ranging from about 4° C. to about 33° C.

Pathogen & pest tolerance: Plants of the new *Sutera* have not been observed to be tolerant to pathogens and pests common to *Sutera* plants.

It is claimed:

1. A new and distinct *Sutera* plant named 'VOLSUT 2302' as illustrated and described.

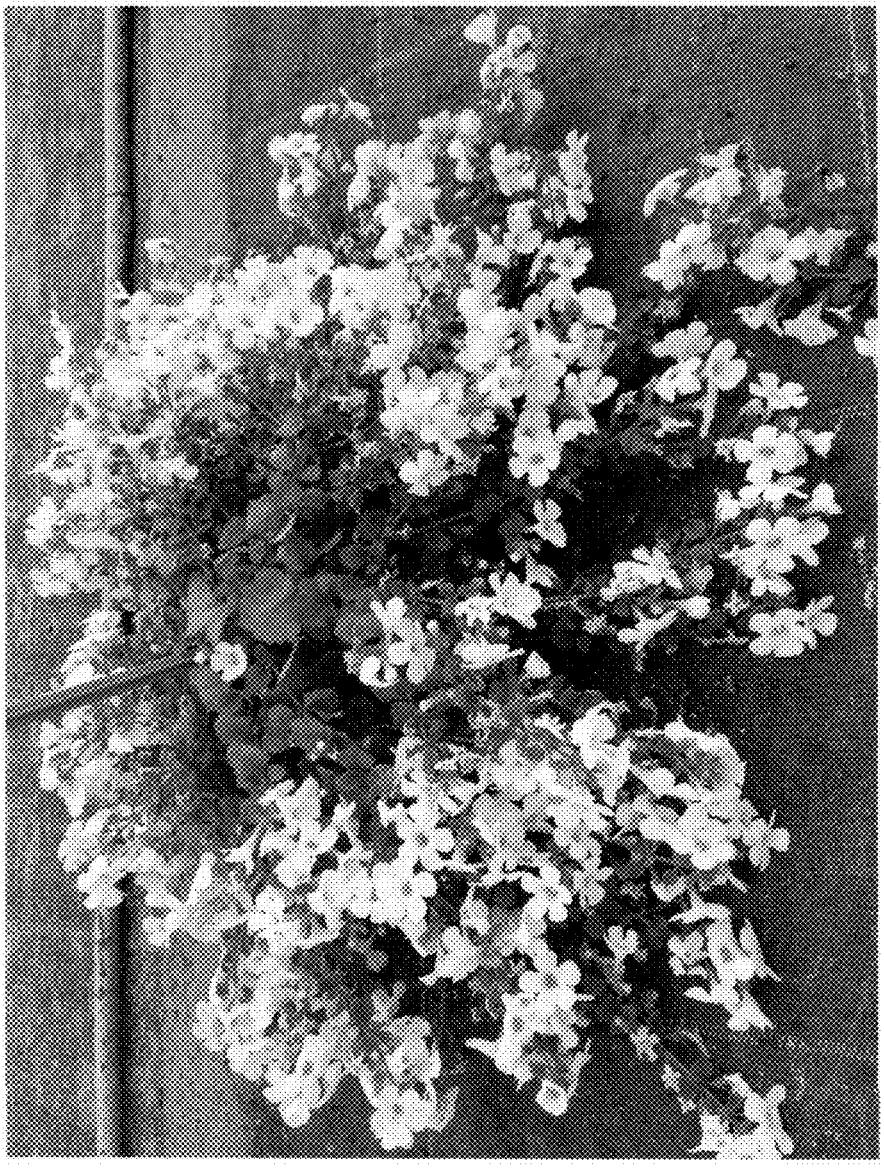

* * * * *